(12) United States Patent
Baudy et al.

(10) Patent No.: US 6,689,905 B2
(45) Date of Patent: Feb. 10, 2004

(54) STEREOISOMERS OF 3-AMINOTRICYCLO [2.2.1.0(2.6)]HEPTANE-1,3-DICARBOXYLIC ACID

(75) Inventors: Reinhardt Bernhard Baudy, Buckingham, PA (US); Jean Yi-ching Sze, Monmouth Junction, NJ (US); Jonathan Laird Gross, Robbinsville, NJ (US)

(73) Assignee: Wyeth, Madison, NJ (US)

( * ) Notice: Subject to any disclaimer, the term of this patent is extended or adjusted under 35 U.S.C. 154(b) by 34 days.

(21) Appl. No.: 10/185,466

(22) Filed: Jun. 27, 2002

(65) Prior Publication Data

US 2003/0018211 A1 Jan. 23, 2003

Related U.S. Application Data

(60) Provisional application No. 60/302,266, filed on Jun. 29, 2001.

(51) Int. Cl.[7] .............................................. C07C 61/12
(52) U.S. Cl. ..................................................... 562/499
(58) Field of Search ........................................ 562/499

(56) References Cited

U.S. PATENT DOCUMENTS 6,124,361 A  9/2000  Chenard

FOREIGN PATENT DOCUMENTS

| EP | 0 363 994 A2 A3 | 4/1990 |
|---|---|---|
| EP | 0 363 994 B1 | 9/1993 |
| WO | WO 99/47490 A1 | 9/1999 |

OTHER PUBLICATIONS

U.S. patent application Ser. No. 10/185,489, Stack et al., Not Published.
U.S. patent application Ser. No. 10/185,445, Greenfield et al., Not Published.
L. Fowden et al., Phytochemistry, 8, 437–443, (1969).
S. Hirsch et al., Pharmacology Biochemistry & Behavior, 56(4), 797–802, (1997).
Y. Hayashi et al., Br. J. Pharmacol., 107, 539–543 (1992).
E. Ndzie, et al., Tetrahedron: Asymmetry, 8(17), 2913–2920, (1997).
J. Monn et al., J. Med. Chem., 42, 1027–1040, (1999).
F. Tellier et al., Bioorganic & Medicinal Chemistry, 6, 195–208, (1998).
F. Trigalo et al., Tetrahedron, 46(15), 5203–5212, (1990).
F. Tellier et al., Bioorganic & Medicinal Chemistry Letters, 5(22), 2627–2632, (1995).
K. Alder et al., Chem. Ber., GE, 93, 2271–2281, (1960).
W. Danysz et al., Behavioral Pharmacology, 6, 455–474, (1995).
A. Carlsson et al., Int. Acad. Biomed. Drug Resch., 4, 118–129, (1993).
E. Frittoli et al., Neuropharmacology, 33(6), 833–835, (1994).
P. Freeman et al., The Journal of Organic Chemistry, 33(6), 2211–2214, (1968).
J. Monn et al., J. Med. Chem., 40, 528–537 (1997).
A. Kozikowski et al., J. Med. Chem., 41, 1641–1650 (1998).

*Primary Examiner*—Paul J. Killos
(74) *Attorney, Agent, or Firm*—Kimberly R. Hild

(57) ABSTRACT

This invention provides a process for the preparation of all four stereoisomers of formula I or a pharmaceutically acceptable salt thereof

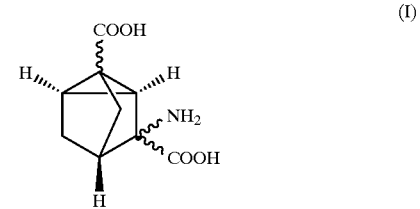

which may be represented by the following structures:

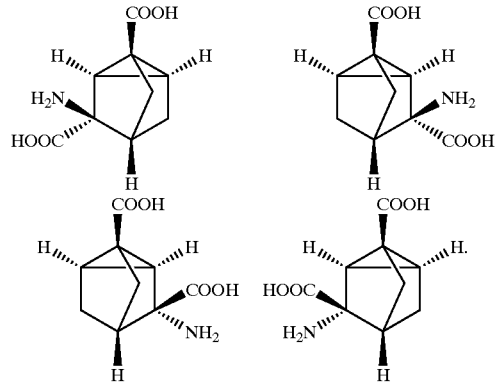

5 Claims, No Drawings

STEREOISOMERS OF 3-AMINOTRICYCLO [2.2.1.0(2.6)]HEPTANE-1,3-DICARBOXYLIC ACID

This application claims priority from co-pending provisional application serial No. 60/302,266, filed on Jun. 29, 2001, the entire disclosure of which is hereby incorporated by reference.

This invention concerns novel stereoisomers of 3-amino-2,6-dimethyl-bicyclo[2.2.1]-heptane-1,3-dicarboxylic acid, as well as methods for their preparation, isolation and use.

BACKGROUND OF THE INVENTION

The Journal of Medicinal Chemistry (1999) 42, 1027–1040 describes the synthesis and pharmacological activity of a series of 4-aminobicyclo[3.1.0]hexane-4,6-dicarboxylic acids (ABHDA's) as group 11 metabotropic glutamate (mGlu) receptor agonists. The (−)-2-oxa-4-aminobicyclo[3.1.0]hexane-4,6-dicarboxylic acid (ABHDA-I) is reported as a mGlu2 agonist with an $EC_{50}$ value of 2.69 nM while the (−)-2-thia-4-aminobicyclo[3.1.0]hexane-4,6-dicarboxylic acid (ABHDA-II) displayed an $EC_{50}$ value of 3.91 nM at the mGlu2 site.

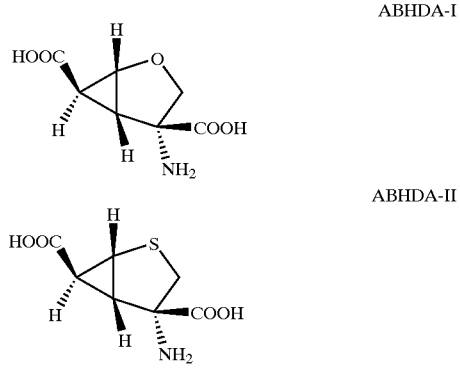

The synthesis and the pharmacological profile of a series of amino-bicyclo[2.2.1]heptane dicarboxylic acids (ABHD's) as rigid analogues of 1-amino-cyclopentane-trans-1,3-dicarboxylic acid (trans-ACPD) is described in Bioorganic and Medicinal Chemistry (1998) 6, 195–208. 2-endo-aminobicyclo[2.2.1]heptane-2-exo-7-anti-dicarboxylic acid (ABHD-I) is reported as a competitive antagonist at the mGlu1a receptor with a $K_b$ value of 300 μM.

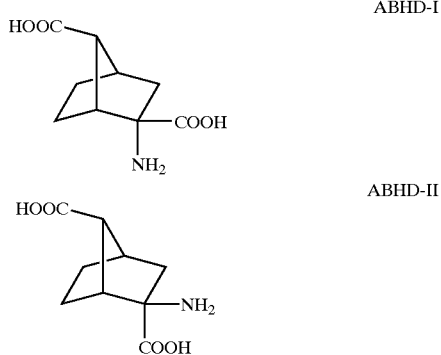

Both compounds (ABHD-I & ABHD-II) are described as agonists at the type 2 mGlu receptors.

Tocris Cookson Inc., 16144 Westwoods Business Park, Ellisville, Mis., 63021 (www.tocris.com) offers lists two isomers of aminotricyclo[2.2.1.0(2,6)]heptane-dicarboxylic acid.

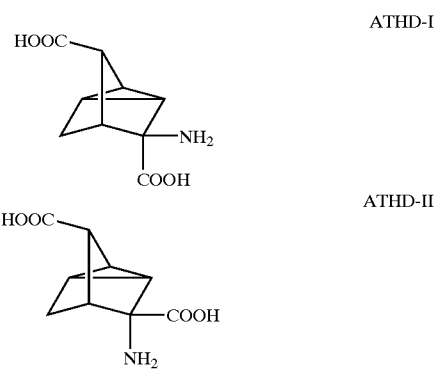

WO 9947490 claims a series of compounds described by the formula below in which n is 0–6, X is $CH_2$, $CH_2CH$ or O, Z is $CHR^2$ or $NR^2$ and $R^1$ and $R^2$ are hydrogen, alkyl, aryl or heteroaryl as metabotropic glutamate receptor ligands useful for the treatment of a variety of neurological and psychiatric disorders.

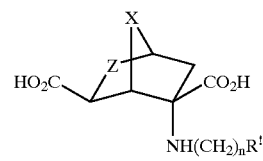

U.S. Pat. No. 6,124,361 (Chenard) teaches substituted bicyclo[3.1.0]hexane compounds of the formula:

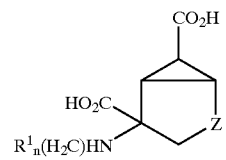

wherein n is an integer from 0 to 6; Z is ($C_1$–$C_4$) alkylene, oxygen, sulfur, NH or N($C_1$–$C_6$)alkyl; and $R^1$ is H or optionally substituted aryl or heteroaryl; which are metabotropic glutamate receptor ligands useful in the treatment of a variety of neurological and psychiatric disorders.

DESCRIPTION OF THE INVENTION

In accordance with this invention, there is provided novel bridged tricyclic 3-aminotricyclo[2.2.1.0(2,6)]heptane-1,3-dicarboxylic acids described by the formula I:

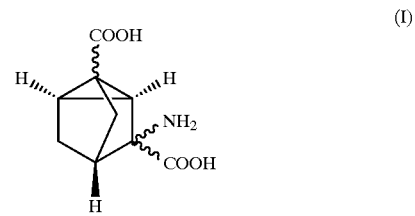

wherein the four stereoisomers may be represented by the following structures

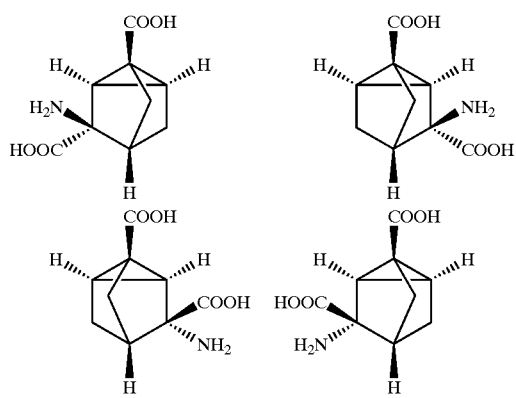

and processes for their preparation.

This invention relates to all four stereoisomers of the bridged tricyclic aminodicarboxylic acid depicted above, as well as pharmaceutically acceptable salt forms thereof. It will be understood that each of the stereoisomers of this invention may be separated and utilized substantially free of their corresponding stereoisomer. Within the scope of this invention, each compound is considered substantially free of its corresponding stereoisomer when the final product comprises greater than 95% of the desired compound, more preferably greater than 98%, most preferably greater than 99.5%. When it is necessary to to distinguish the enantiomers from one another and from the racemate, the sign of the optical rotation [(+), (−) and (+/−)] is utilized. Furthermore, throughout the application, the designations R* and S* are used to indicate relative stereochemistry, employing the Chemical Abstracts convention which automatically assigns R* to the lowest numbered asymmetric center.

Pharmaceutically acceptable salt forms of the four stereoisomers of this invention can also be formed. They include the salt forms derived from such organic or inorganic acids as: hydrochloric, hydrobromic, phosphoric, nitric, sulfuric, acetic, lactic, citric, tartaric, succinic, fumaric, maleic, mandelic, malic, pamoic, propionic, cinnamic, palmitic, itaconic, benzenesulfonic, methanesulfonic, toluenesulfonic and similar known acceptable acids. The compounds of this invention are also capable of forming alkali metal and alkaline earth carboxylates and carboxylates of pharmaceutically acceptable cations derived from ammonia or a basic amine. Examples of the latter include but are not limited to cations such as ammonium, mono-, di-, and trimethylammonium, mono-, di-, and triethylammonium, mono-, di-, and tripropylammonium (iso and normal), ethyldimethylammonium, benzyl-dimethylammonium, cyclohexylammonium, benzylammonium, dibenzylammonium, piperidinium, morpholinium, pyrrolidinium, piperazinium, 1-methylpiperidinium, 1-isopropylpyrrolidinium, 1,4-dimethylpiperazinium, 1-n-butylpiperidinium, 2-methyl-piperidinium, 1-ethyl-2-methylpiperidinium, mono-, di- and triethanolammonium, tris(hydroxymethyl)methylammonium, phenylmonoethanolammonium, and the like.

The compounds of the invention are selective inhibitors of human type 2 excitatory amino acid transporters (EMT-2). Their mode of action causes an increase in synaptic glutamate levels by inhibiting glutamate re-uptake and are useful for the treatment of diseases characterized by glutamate hypofunction, such as schizophrenia, schizoaffective disorder and schizophreniform disorders, with particular effectiveness against the negative symptoms of schizophrenia, and for the treatment of conditions responsive to increased glutamate, such as the cognitive deficits due to aging, stroke, Alzheimer's disease or other neurodegenerative diseases, or schizophrenia. The compounds of the invention are also useful as selective tools for the investigation of excitatory amino acid transport, especially for the identification of agents which selectively stimulate glutamate re-uptake.

This invention provides a process for preparing wherein the four stereoisomers represented by the following structures:

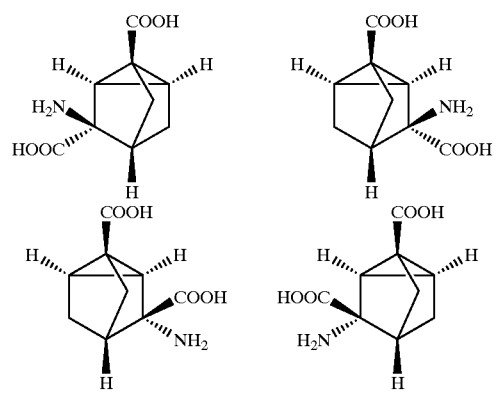

the process comprising the steps of:

1) reacting 2,6-dimethyl-3-oxo-bicyclo[2.2.1]heptane-1-carboxylic acid, having the formula:

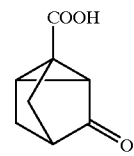

with a chiral alcohol or chiral amine to form the diastereomeric forms of a compound of the formula:

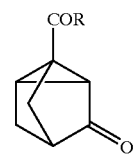

wherein R represents the residue of the respective chiral alcohol or chiral amine;

2) separating the diastereomers using reversed phase chromatography;

3) treating the separated diastereomers from step 2) with ammonium carbonate and an alkali metal cyanide, such as potassium cyanide, in a solvent mixture of organic solvent/water to form spiro-fused hydantoin forms of the diastereomers having the formula:

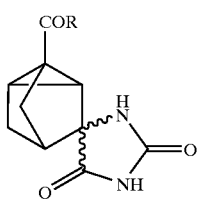

wherein R is as defined above;

4) treating the resulting spiro-fused hydantoin forms of the diastereomers from step 3) with base; and 5) eluting each stereoisomer through an ion exchange column to yield the four aminodicarboxylic acid stereoisomers of the formulae:

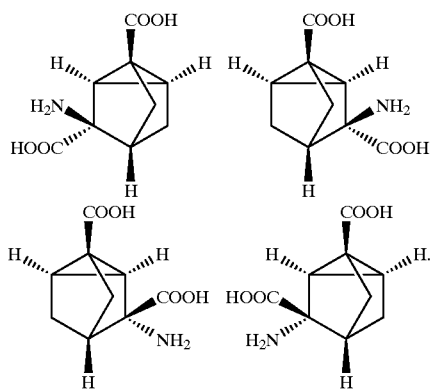

It will be understood that the process steps above may be utilized to prepare all four stereoismeric forms of 3-amino-2,6-dimethyl-bicyclo[2.2.1]heptane-1,3-dicarboxylic acid described above, or the steps may comprise a process for preparing the stereoisomers of one or the other diastereomers separated in Step 2). The process described above also comprises an optional additional step or preparing a pharmaceutically acceptable salt form of one or more of the resulting stereoisomers of Step 5), the step comprising conventional salt formation techniques known in the art, such as treating the resulting stereoisomer with a pharmaceutically acceptable inorganic or organic acid to form a pharmaceutically acceptable acid addition salt form, including those described above.

The reaction of 2,6-dimethyl-3-oxo-bicyclo[2.2.1]heptane-1-carboxylic acid with a chiral ester or chiral amine in step 1), above, may be conducted in conventionally acceptable organic solvents, including including, but not limited to, acetonitrile, acetone, tetrahydrofuran (THF), dimethylformamide (DMF), N-methylpyridine, N-methylpyrrolidone, dimethylsulfoxide (DMSO), sulfalane, $C_1$–$C_8$ alkanols (including methanol and ethanol), glymes, such as monoglyme (1,2-Dimethoxyethane), or $C_2$–$C_8$ glycols. Among the most preferred solvents are DMF, DMSO and N-methyl-pyrrolidone.

In step 2), conventionally known and commercially available chiral columns, such as those available in the Whelk-O 1 line of spherical silica, irregular silica and spherical Kromasil silica columns available from Regis Technologies, Inc., Morton Grove, Ill., U.S.A., or the chiral columns available under the CHIRALCEL® and CHIRALPAK® marks from Merck Eurolab Ltd., may be used.

Step 3) may be conducted in a solvent mixture of an organic solvent and water, preferably at an organic solvent/water ratio of from about 1:1 to about 4:1, more preferably at a ratio of from about 2.5/1 to about 1.5/1, most preferably about 2:1. Acceptable organic solvents are those known in the art to be miscible in water including, but not limited to, acetonitrile, acetone, tetrahydrofuran (THF), dimethylformamide (DMF), N-methylpyridine, N-methylpyrrolidone, dimethylsulfoxide (DMSO), sulfalane, $C_1$–$C_8$ alkanols (including methanol and ethanol), glymes, such as monoglyme (1,2-Dimethoxyethane), or $C_2$–$C_8$ glycols. Among the more preferred solvent systems is a mixture of ethanol and water.

Step 4) may be conducted in water or a mixed organic solvent/water medium, as described above for Step 3). Among the preferred bases for step 4) are the alkali bases known in the art, including barium hydroxide, calcium hydroxide, lithium hydroxide, sodium hydroxide, potassium hydroxide, etc. It will be understood that the concentration of base in this step will effect the time required for completion. Preferably, the concentration of base will be from about 0.1N to the saturation point of the base in the solvent or solvent mixture. More preferably, the base concentration will be 0.5N or higher. A specific example of a useful base is sodium hydroxide at a concentration of from about 1.5 N to about 3.0 N.

Elution of the desired aminodicarboxylic acid stereoisomers in step 5) may be carried out by methods known in the art. Most preferably, the stereoisomers are eluted from the ion exchange column using an acetic acid solution.

In Step 3) of the process above, the ammonium carbonate in the reaction medium is preferably maintained at a concentration of from about 8 mmolar to about 20 mmolar, preferably from about 8 mmolar to about 12 mmolar, and most preferably at about 10 mmolar. The alkali metal cyanide, such as potassium cyanide, in the medium is preferably at a concentration of from about 2 mmolar to about 5 mmolar, preferably between about 2.4 mmolar and about 2.9 mmolar. The reaction volume of ethanol and water is preferably utilized at a concentration of ethanol:water from about 1.75:1 to about 2.25:1, more preferably about 2:1. Step 3) may be conducted at room temperature or with heating. Preferably, heating of the solvent mixture during this step may be from room temperature up to the boiling point of the water in the solvent mixture, though higher temperatures may be utilized under pressure.

In Step 4) of the process, it is preferred that the amount of base, such as sodium hydroxide, utilized be in a stoichiometric molar excess for the reaction in question. More preferably, the base will be present in sufficient concentration to maintain the reaction medium at a pH of 13 or higher. The step may be conducted at a pH of 13.5 or higher.

The elution of stereoisomers in Step 5) may be conducted on conventional or commercially available anion exchange resins, such as the AG 1-X8 ion exchange resin available from Bio-Rad Laboratories, having a corporate headquarters at 1000 Alfred Nobel Drive, Hercules, Calif., U.S.A.

The compounds of formula I can be prepared as illustrated in the scheme below. The starting keto-acid is prepared according Chem.Ber., GE, 93, 1960, 2271–2281 and then derivatized to a suitable chiral ester or amide via a coupling reaction that is accomplished by any of the known amide or ester forming reactions using, but not limited to N,N'-carbonyldiimidazole, bis(2-oxo-3-oxazolidinyl)phosphinic chloride (BOP-CI), N,N'-dicyclohexylcarbodiimide, 1-hydroxybenzotriazole, benzotriazol-1-yl-oxytris (dimethylamino)-phosphonium hexafluorophosphate (BOP) and 2-(1H-Benzo-triazol-1-yl)-1,1,3,3-tetramethyluronium tetrafluoroborate (TBTU). It will be understood by those skilled in the art that commercially available and conventionally known chiral alcohols and amines may be used in the processes of this invention. Among the preferred chiral amines and alcohols which may be used in this process are (R)-(+)-2-amino-3-phenyl-1-propanol, (R)-(+)-α-methyl-4-pyridinemethanol and (R)-(+)-2-phenyl-1-propanol.

Chiral alcohols known in the art may be used in the processes of this invention. Additional examples demonstrating the range of useful chiral alcohols include, but are not limited to, menthol, 2-methoxycyclohexanol, 1-phenyl-1-octyn-3-ol, phenyl-1-napthylmethanol, methyl mandelate, mandel amide, 1-indanol, 1,2-diphenylethanol, 2,2,2-trifluoro-1-phenyl-ethanol, 2-phenylpropanol, 1-phenylpropanol, 1-phenyl-prop-2-yn-1-ol, 1-phenyl-1,3-propanediol, etc.

Chiral amines which may be used herein include the compounds of the general formula $R_1CH(NH_2)(R_2)$ wherein $R_1$ and $R_2$ are independently selected from alkyl of from 1 to 10 carbon atoms, including straight, branched or cyclic alkyl group, alone or in combination, aryl groups, heteroaryl groups or heterocyclic groups. Groups which may be found in these chiral amines are understood to include, but are not limited to cycloalkyl of from 3 to 7 carbon atoms, phenyl, benzyl, napthyl, indane, indole, quinoline, pyridine, pyrimidine, pyrrole, etc. Additional chiral amines or alcohol amines which may be used in the present processes include ephedrine, N-methylephedrine, 2-Amino-1-phenyl-propan-1-ol (norephedrine), quinine, strychnine, brucine, etc.

In the description above, the definition of R as a residue of a respective chiral alcohol or chiral amine is understood to indicate the remaining portion of the alcohol or amine remaining and bound as a portion of the resulting ester or amide.

The resulting mixture of diastereomers is separated using reversed phase chromatography. The separated diastereomers are individually converted to spiro-fused hydantoins by treatment with ammonium carbonate and alkali metal cyanide, such as potassium cyanide, in ethanol/water. The resulting mixture of diastereomers is again separated using a reversed phase chromatography. The resulting four diastereomers are individually hydrolyzed using sodium hydroxide followed by elution through an ion exchange column to yield all four aminodicarboxylic acid stereoisomers.

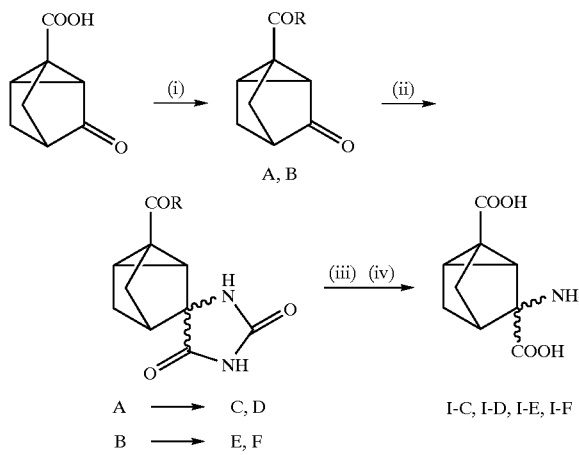

(i) TBTU, suitable chiral alcohol or amine, HPLC, (ii) KCN, ammonium carbonate, MeOH, water, HPLC, (iii) 2N NaOH, (iv) Ion exchange The following examples illustrate a preferred method for the preparation of representative compounds of formula I:

(1 S*,2R*,4S*,6S*)-N-[(1R)-1-benzyl-2-hydroxyethyl]-3-oxotricyclo[2.2.1.0(2,6)]-heptane-1-carboxamide; and (1R*,2S*,4R*,6R*)-N-[(1R)-1-benzyl-2-hydroxyethyl]-3-oxotricyclo[2.2.1.0(2,6)]-heptane-1-carboxamide;

A mixture of 3-oxotricyclo[2.2.1.0(2,6)]heptane-1-carboxylic acid (0.3 g, 1.946 mmole, prepared according Chem.Ber., GE, 93, 1960, 2271–2281), R-(+)2-amino-3-phenyl-1-propanol (0.324 g, 2.141 mmole) and 4-methylmorpholine (0.86 mL, 7.784 mmole) in dimethylformamide (7 mL) was stirred at ambient temperature. 2-(1H-Benzotriazol-1-yl)-1,1,3,3-tetra-methyluronium tetrafluoroborate (TBTU, 0.75 g, 2.335 mmole) was added to the reaction mixture and stirring was continued for 18 hours. The reaction mixture was diluted with ethyl acetate (35 mL), the organic layer separated, washed with 5% aqueous citric acid (2×30 mL), followed by saturated $NaHCO_3$ solution (2×30 mL), and finally washed with brine (50 mL). The organic layer was dried over magnesium sulfate, filtered and evaporated to dryness. Using a reversed phase HPLC (C-18, 8 μM particle size, 41.4 mm and 4.6 mm ID, 25 cm L) column, 10–70% $CH_3CN$/Water, both diastereomers were isolated as light yellow oils in 60% yield. The retention times for the diastereomers A and B were 15.3 min. and 15.8 min., respectively.

A: MS (EI, $M^+$@m/z) 285
B: MS (APCI, $[M+H]^+$@m/z) 286

Spiro-hydantoin Diastereomers of (1S*,2R*,4S*,6S*)-N-[(1R)-1-benzyl-2-hydroxy-ethyl]-3-oxotricyclo[2.2.1.0(2,6)]heptane-1-carboxamide A mixture of (1S*,2R*,4S*,6S*)-N-[(1R)-1-benzyl-2-hydroxyethyl]-3-oxotricyclo-[2.2.1.0(2,6)]heptane-1-carboxamide (A, 0.63 g, 2.207 mmole), ammonium carbonate (1.048 g, 10.091 mmole) and potassium cyanide (0.173 g, 2.648 mmole) was stirred in methanol/water (2:1, 15 ml) at 50° C. for 72 hours. After evaporation of the solvent in vacuo the products were isolated using reversed phase HPLC (C-18, 8 pm particle size, 41.4 mm and 4.6 mm ID, 25 cm L) column, 10–70% $CH_3CN$/water. Both diastereomers were isolated in 31% yield (C) and 53% yield (D) as white solids; mp's A, >260° C. (Decomposition) and B, 167–9° C. The retention times for the diastereomers C and D was 12.6 min. and 13.7 min., respectively.

C: MS (+APCI, $[M+H]^+$@m/z) 356
D: MS (+APCI, $[M+H]^+$@m/z) 356

Spiro-hydantoin Diastereomers of (1R*,2S*,4R*,6R*)-N-[(1R)-1-benzyl-2-hydroxy-ethyl]-3-oxotricyclo [2.2.1.0(2,6)]heptane-1-carboxamide A mixture of (1R*,2S*,4R*,6R*)-N-[(1R)-1-benzyl-2-hydroxyethyl]-3-oxotricyclo-[2.2.1.0(2,6)]heptane-1-carboxamide (B, 0.52g, 1.822 mmole), ammonium carbonate (0.9 g, 9.366 mmole) and potassium cyanide (0.142 g, 2.186 mmole) was stirred in methanol/water (2:1, 15 ml) at 50° C. for 72 hours. After evaporation of the solvent in vacuo the products were isolated using reversed phase HPLC (C-18, 8 μm particle size, 41.4 mm and 4.6 mm ID, 25 cm L) column, 10–70% $CH_3CN$/water. Both diastereomers were isolated in 34% yield (E) and 76% yield (F) as white solids; mp's E, 270–2° C. (Decomposition) and F, 80–2° C. The retention times for the diastereomers E and F were 14.7 min. and 15.3 min., respectively.

E: MS (+APCI, $[M+H]^+$@m/z) 356
F: MS (+APCI, $[M+H]^+$@m/z) 356

General procedure for the preparation of all four stereoisomers of 3-amino-tricyclo[2.2.1.0(2,6)]heptane-1,3-dicarboxylic acid A mixture of the starting spiro-hydantoin-N-[(1R)-1-benzyl-2-hydroxyethyl]-3-oxotricyclo [2.2.1.0(2,6)]

heptane-1-carboxamide (0.5 mmole) and 2N NaOH (3 mL) was refluxed for 20 hours. The reaction mixture was cooled to ambient temperature and washed with dichloromethane (2×20 mL). The aqueous layer was separated and the pH adjusted to 11 using 10% aqueous acetic acid and eluted through an ion-exchange column (Bio-Rad AG1-X8 resin, acetate form, 100–200 mesh). The products were eluted with 1 M acetic acid and the combined fractions were collected and concentrated on a lyophilizer to give the desired stereoisomers as white solids.

(−)-(1R*,2R*,3R*,4S*,6S*)-3-Aminotricyclo[2.2.1.0(2,6)]heptane-1,3-dicarboxylic Acid;

Yield: 98%; MS (APCI, [M+H]$^+$@m/z) 198; mp>260° C. (Decomposition); Optical Rotation (water & NaOH) [α-D]$^{25}$=−32.1°

(+)-(1R*,2R*,3R*,4S*,6S*)-3-Aminotricyclo[2.2.1.0(2,6)]heptane-1,3-dicarboxylic Acid:

Yield: 45%; MS (APCI, [M−H]$^+$@m/z) 196; mp>260° C. (Decomposition); Optical Rotation (water & NaOH) [α-D]$^{25}$=+31.01°

(+)-(1R*,2S*,3R*,4R*,6S*)-3-Aminotricyclo[2.2.1.0(2,6)]heptane-1,3-dicarboxylic Acid:

Yield: 51%; MS (APCI, [M−H]$^+$@m/z) 196; mp>280° C. (Decomposition); Optical Rotation (water & NaOH) [α-D]$^{25}$=+23.980°

(−)-(1R*,2S*,3S*,4R*,6R*)-3-Aminotricyclo[2.2.1.0(2,6)]heptane-1,3-dicarboxylic Acid Yield: 50%; MS (APCI, [M−H]$^+$@m/z) 196; mp>260° C. (Decomposition); Optical Rotation (water & NaOH) [α-D]$^{25}$=−16.0°

The configuration of all four stereoisomers is relative rather than absolute.

What is claimed:

1. A process for preparing stereoisomers represented by the formulae:

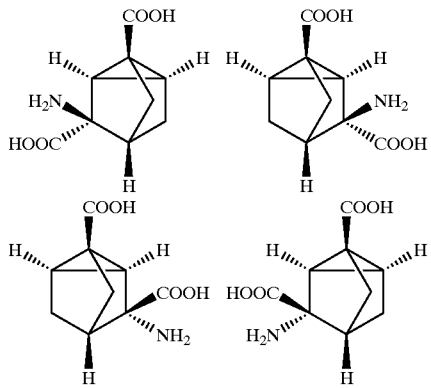

the process comprising the steps of:
a) reacting 2,6-Dimethyl-3-oxo-bicyclo[2.2.1]heptane-1-carboxylic acid, having the formula:

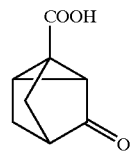

with a chiral alcohol or chiral amine to form the diastereomeric forms of a compound of the formula:

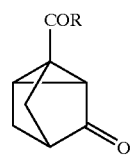

wherein R represents the residue of the respective chiral alcohol or chiral amine;

b) separating the diastereomers using reversed phase chromatography;

c) treating the separated diastereomers from Step b) with ammonium carbonate and an alkali metal cyanide in a volume of organic solvent/water to form spiro-fused hydantoin forms of the diastereomers having the formula:

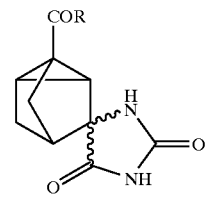

wherein R is as defined above;

d) treating the resulting spiro-fused hydantoin forms of the diastereomers from Step c) with base; and e) passing each stereoisomer through an ion exchange column to yield and separate the four aminodicarboxylic acid stereoisomers of the formulae:

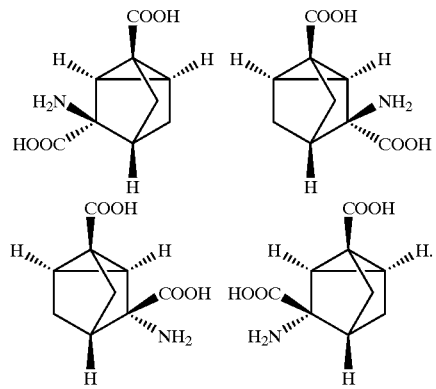

2. The process according to claim 1 wherein the ratio of the volume of organic solvent/water in step c) is between about 1.75:1 to about 2.25:1.

3. The process according to claim 1 wherein the volume of organic solvent/water in step c) is a volume of ethanol/water.

4. The process according to claim 1 wherein the amount of base utilized in step d) is sufficient to maintain the reaction medium at a pH of 13 or higher.

5. The process according to claim 1 wherein the alkali metal cyanide of step c) is potassium cyanide.

* * * * *